March 19, 1957 E. S. BOERNER Plant Pat. 1,578
CHRYSANTHEMUM PLANT
Filed May 16, 1956
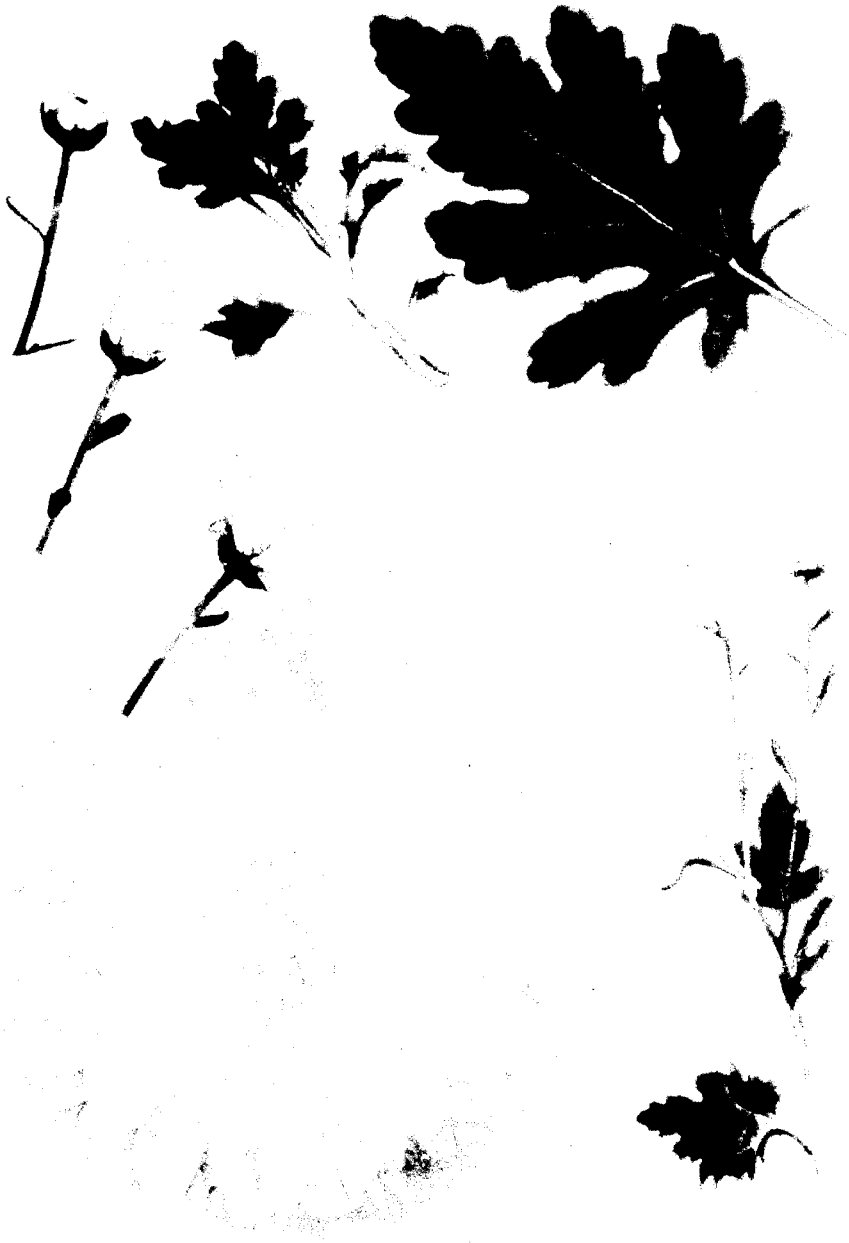
Inventor.
E. S. Boerner
By: Robb & Robb
Attorneys.

United States Patent Office

Plant Pat. 1,578

Patented Mar. 19, 1957

1,578

CHRYSANTHEMUM PLANT

Eugene S. Boerner, Newark, N. Y., assignor to Jackson & Perkins Company, Newark, N. Y., a corporation of New York Application May 16, 1956, Serial No. 585,370

1 Claim. (Cl. 47—60)

The present invention relates to a new and distinct variety of chrysanthemum plant of the incurved type, which was originated by me by crossing an unnamed and unpatented seedling, derived from a cross of "September Dawn" (unpatented) by an unnamed and unpatented large-flowered, golden-colored Hortorum seedling, with the variety "Kingbird" (Plant Patent No. 1,306).

The primary objective of this breeding was to produce a new chrysanthemum variety having in combination the growth and vigor of the parent variety "Kingbird" and large flowers of the incurved type of "September Dawn" and the Hortorum seedling antecedents. This objective was fully achieved, as evidenced by the fact that my new variety is characterized by its upright and vigorous growth, and by large flowers of the incurved type which is uncommon in other hardy chrysanthemums.

The foregoing characteristics and distinctions definitely differentiate my new variety from its parents, as well as from all other varieties of its class, and asexual reproduction of the new variety by both top cuttings and underground runners, as performed at Newark, New York, shows that these characteristics and distinctions come true to form and are established and transmitted through succeeding propagations.

The accompanying drawing shows typical specimens of the vegetative growth and flowers of my new variety in different stages of development, and as depicted in color as nearly true as it is reasonably possible to make the same in a color illustration of this character.

The following is a detailed description of my new variety, with color terminology in accordance with Ridgway's Color Standards and Nomenclature:

Parentage: An unnamed seedling of "September Dawn" × an unnamed large-flowered, golden-colored Hortorum seedling × "Kingbird."

Classification: Incurved.

Growth: Vigorous; strong; medium height.

Cold resistance: Winter hardy in northern New York.

Blooming period: In the Newark, New York, climatic area, blooming usually begins about September 30th and continues until freezing.

*Flower*

(Observations made from specimens grown in a field at Newark, New York, in the early part of October, and in the early morning.)

Bud:

*Color.*—When sepals first divide—Light Chalcedony Yellow, Plate 17. When petals begin to unfurl—Empire Yellow, Plate 4. When half-blown: inside—Light Cadmium, Plate 4, lightly overcast with Lemon Chrome, Plate 4; outside: Empire Yellow, Plate 4.

*Peduncle.*—Strong. Color—Light Cress Green, Plate 31.

Bloom:

*Size.*—From 5 to 5½ inches.

*Stem.*—Long; strong.

*Form.*—Incurved.

*Petalage.*—Double.

*Color.*—Center of flower—Light Cadmium, Plate 4. Outer petals—Pinard Yellow, Plate 4, lightly overcast with Pale Greenish Yellow, Plate 5. Base of petals—Pale Green Yellow, Plate 5. Inside of petals—Pinard Yellow, Plate 4, lightly overcast with Empire Yellow, Plate 4. Reverse of petals—Empire Yellow, Plate 4.

*Petals.*—Texture—stiff. Form—oval.

*Fragrance.*—Characteristic chrysanthemum.

*Plant*

Form: Upright.

Growth: Medium height.

Foliage:

*Size.*—Large.

*Quantity.*—Normal.

*Color.*—Upper side—Dark Cress Green, Plate 31. Reverse side—Light Bice Green, Plate 17.

*Texture.*—Leathery.

I claim:

A new and distinct variety of chrysanthemum plant of the incurved flower type, substantially as herein shown and described, characterized particularly as to novelty by its upright and vigorous habits of growth, the large size of its flowers, and the distinctive color of its flowers.

No references cited.